United States Patent [19]

Lee et al.

[11] Patent Number: 5,334,386

[45] Date of Patent: * Aug. 2, 1994

[54] METHOD OF CONTROLLING ZEBRA MUSSELS

[75] Inventors: Harold H. Lee, Lambertville, Mich.; Peter C. Fraleigh, Sylvania, Ohio; Aklilu Lemma, Florence, Italy

[73] Assignee: The University of Toledo, Toledo, Ohio

[*] Notice: The portion of the term of this patent subsequent to Oct. 12, 2010 has been disclaimed.

[21] Appl. No.: 928,291

[22] Filed: Aug. 12, 1992

Related U.S. Application Data

[63] Continuation of Ser. No. 596,879, Oct. 12, 1990, Pat. No. 5,252,330.

[51] Int. Cl.⁵ .......................... A61K 35/78; C02F 1/68

[52] U.S. Cl. .................. 424/195.1; 210/749; 210/755

[58] Field of Search ............... 424/195.1; 210/755, 210/749

[56] References Cited

PUBLICATIONS

Duncan, J., The Toxicology of Plant Molluscicides, Pharmac Ther vol. 27 pp. 243–264, 1985.
Dorsaz, A., Further Saponins from *P. dodecandra* . . . , Planta Medica O (6) 1986 pp. 557–558.
Adewunmi, C., Comparative Evaluation of the Molluscicidal . . . Fitoterapia vol. 58 #5 1987 pp. 325–328.

*Primary Examiner*—Michael G. Wityshyn
*Assistant Examiner*—Ralph Gitomer
*Attorney, Agent, or Firm*—Marshall & Melhorn

[57] ABSTRACT

Zebra mussels are controlled by contacting them with the active portion of a Phytolacca plant.

11 Claims, 1 Drawing Sheet

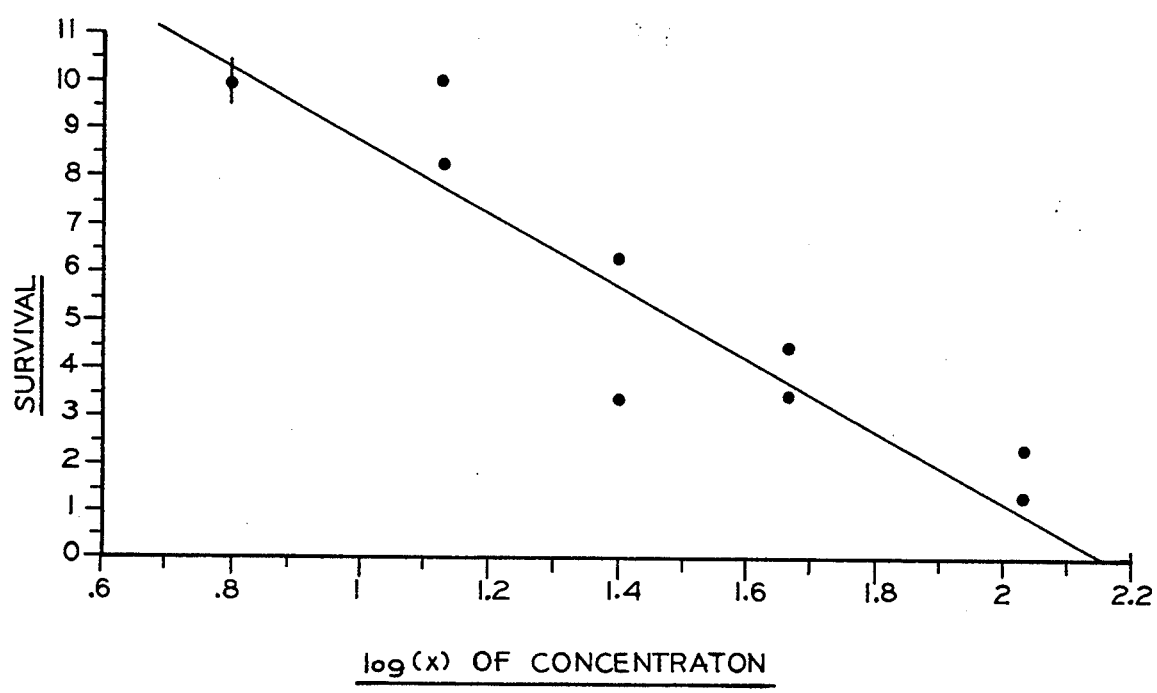

METHOD OF CONTROLLING ZEBRA MUSSELS

This application is a continuation of application Ser. No. 07/596,879, filed Oct. 12, 1990, now U.S. Pat. No. 5,252,330.

TECHNICAL FIELD

The present invention relates to the Zebra mussel (*Dreissena polymorpha*) and more specifically it relates to controlling Zebra mussels in water intakes and cooling systems by a chemical treatment.

BACKGROUND ART

An undesirable bivalved mollusc, *Dreissena Polymorpha*, commonly known as a Zebra mussel is infestating the Great Lakes and its tributaries. It is estimated that over the next ten years this Zebra mussel invasion may cost $2 billion to $5 billion. This problem is especially severe in Lake Erie.

The mussels attach and cluster firmly on the intake pipes and grating systems associated with water intakes. This is done by the mussels generating a tuft of fibers known as byssae, or byssal threads, which protrude through their hinged shell and attach to any subsurface with an adhesive secretion to tenaciously anchor them in place. Any firm surface will be colonized by the Zebra mussel including rock, metal grating, wood, glass and so forth. All that is required is for the surface to be hard. Thus the Zebra mussels adhere to the auxiliary equipment associated with water intake and cooling systems and firmly attach and then form large clusters and layers. This obviously ends up severely reducing the water flow. One utility company has been reported to have had a reduction in the water systems' intake capacity from 210 million gallons a day to 150 million gallons a day as a result of the attachment and clustering of the Zebra mussels. Another water department was incapacitated in December, 1989 because of a combination of ice and significantly reduced capacity of the water intake pipes resulting from Zebra mussel infestation.

This problem caused by Zebra mussels needs a solution.

SUMMARY OF THE INVENTION

Applicants have now solved the problem. In accordance with the present invention a method of controlling Zebra mussel is provided which comprises contacting the mussels with an effective lethal amount of treating medium comprising a molluscicidally effective portion of a Phytolacca plant and most desirably *Phytolacca dodecandra*.

In practicing the present invention the contacting of the Zebra mussels with the treating medium may be effected for a sufficient period of time to kill the Zebra mussel with its consequent loss of attaching and clustering strength or the contacting may be discontinued prior to the death of substantially all of the mussels being contacted but conducted for a sufficient period of time that the surviving Zebra mussels have been weakened as to their ability to attach to a substrate and to cluster with each other or both. In the latter instance, because of the weakening of the clustering and attaching tendencies, removal of the Zebra mussels is much easier than under the present state of the art.

In addition to the physiological response of weakening the ability to attach to a substrate and cluster, especially with adult Zebra mussels, even while alive, another physiological response of the mussels has been noted. That is, there is an effective exposure time to treatment in accordance with the invention after which there is an irreversible physiological response which results in later death. Thus in another embodiment, the mussels are treated for the effective exposure time to place them in that irreversible state, then the treatment is discontinued. Operation, for example at the water intake, continues. Subsequently the latent death occurs and then these Zebra mussels can be removed from the system.

Thus as will be apparent, when the term effective lethal amounts of the treating medium is used the term comprehends, unless indicated to the contrary, more than treating the Zebra mussel to kill it while the treatment is in effect. It also comprehends treatment whereby the Zebra mussels are placed in a condition of latent death which is effected later, and also comprehends causing the Zebra mussels to be placed in a state whereby they have a lower strength with regard to their ability to attach and to cluster. Thus the term lethal includes not only fatality during treatment, but also creating an irreversible condition of imminent death. It further includes what might be referred to as placing the mussels in a debilitated state because of the weakening of their ability to adhere and cluster.

BRIEF DESCRIPTION OF THE DRAWING

The Figure represents a plot of the survival rate of mussels at different concentrations of extract.

DETAILED DESCRIPTION OF THE INVENTION INCLUDING THE BEST MODE OF CARRYING IT OUT

Representative Phytolacca include *P. acinosa, P. americana, P. brachystachys, P. dioicao, P. esculenta, P. ligida, P. octandra, P. rivinoides,* and *P. rugose*. Preferably, the source of the molluscicidally effective ingredient contemplated for use in the present invention will be that from *Phytolacca dodecandra* generally known as Endod whose usefulness in the control of snails in Ethiopia and other African countries is known. This material is biodegradable. In the preferred use of *Phytolacca dodecandra*, the treating medium may be formed by simply grinding dried berries and suspending the powder in water. A butanol extracted portion, such as that obtainable in accordance with the teachings of U.S. Pat. No. 3,813,383 may be employed. Finally a concentrate can be used which is prepared by a process which comprises water extraction, filtration and then drying of the filtrate or supernatant liquid to obtain the desired concentrate powder. The latter type material will be referred to hereinafter as Endod-P and is prepared essentially by soaking finely ground berries overnight in warm water and then filtering the material. The filtrate is then freeze dried or spray dried to obtain the active solid extract. The filtrate should generally be dried at low temperatures that is below 40° C. and, since the extract is hydroscopic, it should be stored then in an airtight container.

When employed as the treating agent in water, the amount of such concentrate generally should be between about 5 ppm to about 20 ppm.

When the treating medium is formed from a suspension of ground *Phytolacca dodecandra* berries, it is preferred that the suspension, either after the final treating material is formed or, if a stock material is first formed, then the stock be subjected to an incubating step. This can be simply effected by heating over about a 15 minute period to about 30° or 35° C. or slightly higher. It may likewise be effected by holding at an elevated temperature such as 30° to 40° C. for about an hour or two or by simply allowing the suspension to sit overnight (about 16 hours) at about room temperature. The incubated material will preferably be used within about a 24 hour period because after that time its activity decreases. However the incubated material may be held at about 4° C. without significant loss of potency.

The effective toxin as contemplated in the present invention is a saponin which has generally been designated Lemmatoxin. Its structural formula is set forth in British Specification 1,277,417, page 1, line 70.

Generally when contacting or treating the Zebra mussels as contemplated herein, the contacting or treatment will be done for at least about 4 hours and typically 4 to 8 hours or even more. This will desirably allow an irreversible physiological response to take place which ultimately will result in the death of a substantial number of the mussels or in their becoming debilitated with respect to attachment and/or clustering ability. Because of cost considerations and convenience it is preferable to use as the treating medium, an aqueous suspension of the ground Endod berries in a concentration of at least 5 ppm and to about 20 ppm.

While the above describes the present invention in sufficient detail to allow those skilled in the art to make and use same, nonetheless further exemplification of the invention follows. It is to be understood that these examples are not limiting but are simply presented to facilitate others making and using the present invention.

In the following, berries from *Phytolacca dodecandra* were employed to provide the chemical agent to control the Zebra mussel. These berries were obtained from Addis Ababa University in Ethiopia (Institute of Pathobiology type 44). As previously indicated, these berries are also known as Endod berries. In the Examples which follow reference will be made to the ability of the Zebra mussels to attach by their byssal threads to a substrate such as, for example, a beaker in the laboratory, or in the real environment, for example the grating at water intakes. This attachment will occasionally be referred to as "attaching" or sometimes abbreviated as simply "A". Reference will also be made to clustering. Clustering refers to the aggregation of the mussels upon themselves. Thus, as will be apparent, the attaching tendency of the mussels is more the nature of their adhesive ability whereas the clustering tendency is more of a cohesive tendency. Clustering will be referred to as such or may be abbreviated as "C".

PHASE I

Example I

The following Example will generally show that when used in effective lethal amounts the present invention can be effective in killing the Zebra mussel. Additionally, the Example shows that by treatment in accordance with the invention, the ability of the Zebra mussel to attach to a substrate can be virtually eliminated or at least inhibited or retarded. The Example also illustrates the delayed activity of the present treatment and the existence of what is termed an effective exposure time (EET), that is a time beyond which treatment is not needed and which creates an irreversible physiological response in the mussels, resulting, ultimately, in death or a reduction in their ability to attach and/or cluster.

In the following example, dried berries of *Phytolacca dodecandra* (Endod plant) which were reddish gold or rust colored in appearance were coarsely ground in a mortar and pestle. The material was then made into a 1% by weight master batch of the ground berries in bubbled tap water and the master batch was heated over a fifteen minute period to 36° C. This master batch was then diluted with tap water which had been air bubbled for about twenty-four hours to produce 4 treating media respectively containing 2500 parts per million (ppm), 625 ppm, 156 ppm and 39 ppm of the dried, ground Endod berry. The Zebra mussels were contacted with the treating medium by immersing ten different Zebra mussels in each of the four treating media (500 ml beakers containing about 200 ml of the treating medium). This procedure was duplicated and in one series of experiments air was bubbled through the treating medium during the time the mussels were immersed in the treating medium therein and in the other experiment no air was bubbled through the medium. In each case a control sample was also used in which the treating medium was simply the air-bubbled tap water. After about 24 hours the Endod containing treating media were all discarded and fresh water was then added so the mussels were no longer in contact with the Endod medium.

The results of this testing are summarized in Table I below.

TABLE I

| ppm | 24 Hrs. | 40 Hrs. | 48 Hrs. | 61 Hrs. |
|---|---|---|---|---|
| WITH AIR BUBBLING | | | | |
| 2500 | 9 Dead | All Dead | | |
| 625 | 8 Dead | All Dead | | |
| 156 | 8 Dead | All Dead | | |
| 39 | 0 Dead | 6 Dead | 8 Dead | 9 Dead |
| Control | 5A, None Dead | 1 Dead | 3A, 9 Living | 9 Living 4A |
| WITHOUT AIR | | | | |
| 2500 | 8 Dead | All Dead | | |
| 625 | 9 Dead | All Dead | | |
| 156 | 8 Dead | All Dead | | |
| 39 | No Dead 3A | 1 Dead | 8 Survived 0A | 7 Survived |
| Control | 1 Dead, 4A | 9 Living | 9 Living 4A | 9 Living 9A |

The effective exposure time is especially well demonstrated in this experiment with the bubbled air at the 39 ppm level. Note that no Zebra mussels were dead after the 24 hour treatment, and when the water was changed, but after 48 hours (24 hours in fresh water not containing any Endod) the delayed activity resulted in the latent deaths of eight Zebra mussels (6 after 40 hours). Death means that the shells are open and the mussels are non-responsive (shells stay open) upon touching or moving. With the bubbling air, there was virtually no tendencies for the mussels to attach (A) to the beaker whereas in the control there was such a tendency. Note also the much greater tendency for the untreated Zebra mussels in the controls to attach compared to those contacted with the treating medium.

PHASE II

Example II

The general procedure of Example I was repeated with the following modifications. Instead of simply heating the master, or stock, solution prior to dilution over about a fifteen minute period to 36°, the master solution was heated to a temperature of 37° C. and held there for approximately one hour to incubate the treating medium. Additionally 150 ml of the respective treating media were employed and there was no change from the Endod treating media to fresh clean water as was done in Example I. Air bubbling was employed during the contact time with the treating medium.

After approximately 24 hours all ten of the mussels had died in the 2500 ppm suspension. Six of the ten and eight of the ten respectively died in the 625 ppm and 156 ppm solution. The 39 ppm solution killed eight mussels after the 22 hour period. The result with regard to the 39 ppm solution shows that the longer incubation or fermentation step provides a more active toxin(s) since it will be noted in Table I that no Zebra mussels were killed at 39 ppm after 24 hours. After about 38–39 hours, all mussels in the treating media were dead. The control showed one mussel death after the 38–39 hours.

Example III

Example II was generally repeated except the solution prior to dilution was incubated at about 37° C. for about two hours and the treating solutions were respectively 100 ppm, 50 ppm, 25 ppm, and 12.5 ppm. Again no change to fresh water was made during this evaluation. Table II below summarizes the results.

TABLE II

| ppm | 7 Hours | 22 Hours | 47 Hours | 94 Hours |
|---|---|---|---|---|
| 100 | 10 Alive | 2 Alive | 0 Alive | — |
| 50 | 10 Alive | 3 Alive | 0 Alive | — |
| 25 | 10 Alive | 9 Alive | 1 Alive | 1 Alive |
| 12.5 | 10 Alive | 10 Alive | 10 Alive | 6 Alive |
| Control | 10 Alive | 10 Alive | 10 Alive | 9 Alive |

This shows that a concentration of 25 ppm – 50 ppm is desirable when using the reddish gold Endod berry.

PHASE III

In the following experiments, unless otherwise indicated, green *Phytolacca dodecandra* berries (type 44 from Addis Ababa University) were ground and passed through a 250 micron sieve (later referred to as 250 micron powder) and used to provide the molluscicidally effective material.

Example IV

The *Phytolacca dodecandra* (250 micron powder) was added to water to prepare a stock treating medium of 1000 ppm using air bubbled tap water. This suspension was allowed to incubate at room temperature for about sixteen hours and then was refrigerated for approximately 24 hours until use. The suspension was then diluted with additional aerated tap water to form treating suspensions (200 ml) respectively of 100 ppm, 50 ppm, 12.5 ppm, and 6.25 ppm. A control was also employed. Ten different Zebra mussels were immersed in each of the five treating media. This procedure was then duplicated and the results of the testing are set forth in Table III below. The numbers indicate the number of surviving mussels. The numbers in the parenthesis indicate the number of those which are alive that were attaching (A).

TABLE III

| | | (Numbers Indicate Those Alive) | | | | |
|---|---|---|---|---|---|---|
| ppm | Day #1 Start | Day #1 6:25 pm | Day #2 10:30 am | Day #2 4 PM | Day #3 4:30 pm | Day #3–4 |
| 100 | 10:45 am | 1 | 0 | | | |
| | 11:00 am | 2 | 0 | | | |
| 50 | 10:45 am | 4 | 0 | | | |
| | 11:00 am | 3 | 0 | | | |
| 25 | 10:45 am | 3 | 0 | | | |
| | 11:00 am | 6 | 0 | | | |
| 12.5 | 10:45 am | 8 | 5 | 2 | 0 | |
| | 11:00 am | 10 | 3 | 1 | 0 | No Attach-ment |
| 6.25 | 10:45 am | 10 | 7 (2A) | 4 | 1 | |
| | 11:00 am | 10 | 6 (2A) | 3 | 2 | |
| Control | 10:45 am | 10A | 10A | 10A | 10A | Cluster |
| | 11:00 am | 10 (8A) | 10A | 10A | 10A | |

After the observation at 10:30 AM on Day 2 the Zebra mussels were removed, washed and put into fresh aerated water. The dead Zebra mussels were included.

The effective exposure time is apparent in Table III. That is note, for example, with the 12.5 ppm treating medium, at Day 3, all the Zebra mussels that had been alive when the water was changed were now dead. Also observe with regard to the 6.25 ppm treating suspension that, while the animals were beginning to attach at day two, after the treatment was discontinued and the mussels put in fresh water, additional animals died and also observe that of those that survived there was no attachment- This shows that even if a fatal dosage is not employed, the present treatment inhibits or retards the attachment strength and propensities of the Zebra mussel. Such a decrease in the attachment capabilities of the Zebra mussels, as will be readily apparent to those skilled in the art, significantly improves the economics of the operation of water treating facilities. Shutdowns will not be necessary. Mussels will come loose, be carried down the pipe and then collected at the end of the pipe.

Attached Graph A is a dose-response plot of the data of Table III. Graph A represents a plot of the animals which survive at 6:25 p.m. on Day 1, or about eight hours after immersion in the treating medium. Thus the Y axis in the plot shows the number of animals which survive out of ten after about 8 hours. The X axis in the plot is a plot of log (x) where x is the concentration of the *phytolacca dodecandra* powder in the treating medium in milligrams per liter of treating medium (6.25 ppm approximately corresponds to log x of 0.8 and 100 ppm approximately corresponds to log x of about 2) . Thus it will be seen in Graph A that $LC_{50}$ is approximately a concentration of $10^{1.5}$ (miligrams per liter) i.e. between 25 ppm – 50 ppm.

Example V

Endo-P, which was described above, was dispersed in air-bubbled water to produce a stock suspension of 1000 ppm. This was then used, without incubation, to provide treating media of 50, 25, 12.5, 6.25 and 3.125 parts per million. A control was also employed. Ten different Zebra mussels were dispersed in each of the treating solutions. After approximately 22-23 hours, when the first observation was made, all mussels in the 50 ppm, 25 ppm and 12 ppm treating media were dead. In the 6.25 ppm treating medium one mussel was alive in one instance and none in another instance.

In duplicate runs using the 3.125 ppm treating medium in both instances all ten mussels were alive after the 22-23 hour period, but in one instance all ten were attaching to the beaker. In the control all mussels were alive. After the 22-23 hour time period, the mussels were removed and washed and fresh water was employed (no treating medium) for the 6.25 ppm, the 3.125 ppm and the control samples. After about 68-69 hours the mussel in the 6.25 ppm treating medium was still alive but died after about 87-88 hours. The mussels in the duplicate runs of the 3.125 ppm treating media were still alive after about 68-69 hours; after about 87-88 hours they were now clustered. This shows that treating with the 3.125 PPM treating medium was not satisfactory and was too dilute. The mussels in the control were also clustered after the 87-88 hours.

Example VI

A. The above Endod-P (no incubation) was formulated into a treating medium of, in one case, 5 ppm and 2.5 ppm in another. Ten Zebra mussels were then immersed in the two Endod-P treating media. After approximately 46.5 hours it was observed that all the mussels in the 5 ppm treating medium were dead. The mussels in the 2.5 ppm aqueous treating medium were all alive and exhibited only light attachment to the glass beaker.

B. Treating media using the 250 micron powder of 10 ppm, 5 ppm and 2.5 ppm were made. Prior to dilution to these concentrations the stock solutions were incubated about 16 hours at room temperature- Ten different Zebra mussels were immersed in each of the treating media. After approximately 46½ hours all mussels in the 10 ppm treating medium were dead. One was dead in the 5 ppm medium but it was observed with the rest there was no attachment to the glass. The animals put into the 2.5 ppm treating medium clustered.

The foregoing clearly shows that even without killing the Zebra mussel its ability to attach and form clusters is significantly weakened by treatment in accordance with this invention.

C. After the approximate 46.5 hour time period noted in A and B above, the treating media were removed, the mussels washed and placed in fresh water. In all instances where there were live mussels (2.5 ppm with Endod-P and both 2.5 ppm and 5 ppm with the 250 micron powder) after approximately 19 additional hours no additional mussels had died and the mussels formed clusters. This indicates the reversible nature of the treatment if these mussels are not treated with a sufficient amount of the treating medium. Thus the concentration of the Endod-P material should desirably be at least 5 ppm. The concentration of the ground Endod berry (250 micron material) in the dispersion desirably should be at least 10 ppm.

Example VII

The present experiment shows the ability to treat Zebra mussels in Lake Erie water with sufficient amounts of the treating medium to kill them and also illustrates that, even if all the Zebra mussels are not killed, their propensities to adhere and cluster are significantly weakened.

The above 250 micron powder was employed to make duplicate treating media in Lake Erie water of 50 ppm, 25 ppm, 12.5 ppm and 6.25 ppm of powder. The stock material prior to the various dilutions was incubated at room temperature for about 16 hours. A control was also used. After approximately 26-27 hours, the ten mussels in the control were still alive and after approximately 48 hours they had clustered into two groups. After the 26-27 hour time period the mussels in both of the 6.25 ppm treating media were still alive and after 48 hours had clustered and attached to the beaker. In the duplicate runs made with the 12.5 ppm treating medium, five mussels were alive both after the 26-27 hour time period and the 48 hour time period in one instance, and six mussels at both times in the other instance. It was noted that these five and six survivors however did not cluster or attach to the beaker. This shows the ability to kill some of the mussels while at the same time weakening the attachment and clustering ability of the survivors. Thus, for example, in this instance after treatment for approximately 26-27 hours with the 12.5 ppm treating suspension, all mussels, whether alive or dead, can be more easily removed from the infested area.

In all instances all Zebra mussels treated with the 25 ppm and 50 ppm treating media of 250 micron powder were dead after 26-27 hours.

Example VIII

This example further demonstrates the effective exposure time.

A treating medium of 50 parts per million of the 250 micron powder was made using a stock suspension which had been incubated about 16 hours at room temperature. Fifty Zebra mussels were immersed in the 50 ppm medium. At the end of 1 hour ten mussels were removed, washed and placed in fresh water. At the end of two hours another ten mussels were removed, washed and put into fresh water. Similarly, after the end of 4 hours an additional ten were so treated and at the end of approximately 8 hours an additional ten mussels were so treated- After a total elapsed time of approximately 24 hours, it was observed that all of the remaining twenty Zebra mussels which had not been removed from the treating medium were dead. At the end of the 24 hour period all of the mussels which had been subjected to the 1 hour treatment (23 hours in fresh water), the 2 hour treatment (22 hours in fresh water) and the 4 hour treatment were alive and attaching to the wall of the beaker. At the end of 24 hours, four of the mussels which had been subjected to the 8 hour treatment (16 hours in fresh water) had died. Of the surviving four Zebra mussels which had been subject to treatment for 8 hours, only one was showing signs of attachment and this attachment was weak thereby showing the ability to weaken the attaching strength even prior to death.

The procedure as above was repeated except the treating medium contained 25 parts per million of the 250 micron powder. After the 24 hour period the Zebra mussels which had been subject to the treatment for 1, 2 and 4 hours respectively were all still alive and were attaching and clustering to the beaker walls. After the 24 hour period three of the ten Zebra mussels that had been subjected to the 8 hour treatment in the 25 ppm treating medium survived and were not attaching.

Seven of the twenty mussels treated for 24 hours at 25 ppm survived (65% killed).

It will be seen that a minimum treatment time of 4 hours is required and, preferably, one of about 8 hours so in that treatment time a substantial amount, (40%, and 70%) are killed and the survivors have a lesser propensity to further attach and aggregate and create clusters.

The foregoing as indicated also exemplifies the latent death of the Zebra mussels, that is, the existence of an irreversible physiological response of some of the mussels which results in their later death. Upon removal of the mussels from the treating medium at the 8 hour period all ten mussels in each instance were alive. With regard to the 25 ppm treating medium it will seem that the effective exposure time resulting in the death in 24 hours of at least 50% of the mussels is between 4 and 8 hours. More specifically the 25 ppm treating solution shows that a treating time of about 8 hours results in a 70% kill after 24 hours. In this experiment a 40% kill resulted with the 50 ppm treatment.

Example IX

Three different runs were made at treating suspension concentrations of 20 ppm, 10 ppm, 5 ppm and 2.5 ppm with the treating material being the 250 micron powder from a stock suspension which had been incubated at room temperature overnight (about 16 hours). In each instance ten Zebra mussels were evaluated. After a 24 hour period the number of surviving mussels in the 20 ppm treating medium were respectively 0, 0, and 1. The survivors for the 10 ppm treating medium were respectively 5, 3, and 7. The number of survivors for the 5 ppm solution were respectively 9, 9, and 10. At 2.5 PPM all mussels survived after 24 hours.

Thus it will be seen from the above that the lethal concentration (LC) to kill 50% of the mussels in a 24 hour period is greater than 5 ppm (at room temperature) and greater than 10 ppm for a greater probability of killing 50% of the mussels. Similarly, the LC for a 100% kill at room temperature over a 24 hour period is greater than 10 ppm and greater than 20 PPM for a significantly higher probability of 100% kill.

After the 24 hour treating period, the mussels were removed from the treating medium, washed and then put into fresh water and observed several (5) days later. The results showed with the initial 2.5 ppm treatment, there were no significant latent deaths after the mussels were placed in fresh water, hence indicating that in order to provide for the irreversible physiological response of the mussels which results in a later death, the treating medium must be at least 2.5 ppm and preferably greater than 5 ppm.

Example X

Treating media 100, 50, 25, and 12.5 ppm in water of the 250 micron powder were similarly prepared. The treating media were cooled to between 4° C.–10° C. and ten Zebra mussels were immersed in each of the treating media. Table IV below summarizes the results and shows the number of surviving mussels. After the 96 hour period at 4° C.–10° C., the mussels were removed and washed and then put into fresh water at room temperature. It will be observed that three days later all the surviving mussels had clustered and recovered. Thus it will be seen that at cold water temperatures the effectiveness of the treatment is not nearly as good as the examples above which were generally done at about room temperature (25° C.). For most effective treatment therefore the aqueous treating medium should be in excess of about 10° C. In Table IV below "detach" means that all the mussels had survived but they were not attaching to the beaker.

TABLE IV

| | (8/20/90) 4° C. Treatment | | | | |
|---|---|---|---|---|---|
| PPM | 22 Hrs | 42 Hrs | 72 Hrs | 96 Hrs | 7 Days |
| 100 | Detach | Detach | 6 | 5 | RECOVER |
| 50 | Detach | Detach | 3 | 3 | CLUSTER |
| 25 | Detach | Detach | 5 | 5 | |
| 12.5 | Detach | Detach | 6 | 5 | |
| Control | Detach | Detach | Detach | Detach | |

The present invention will be most expeditiously exploited by introducing the effective controlling amounts of the treating medium which comprises the molluscicidally effective portion (a saponin) of a Phytolacca plant in predetermined amounts at the water intake (or in a cooling system) for predetermined periods of time. Since the volumetric water flow is known, the amounts to be added will be routinely calculated by those skilled in the art. Any conventional pumping mechanism may be employed to introduce the aqueous treating medium in the form of a concentrate. Because of the biodegradable nature of the materials employed they will not have a persistent adverse ecological effect.

While the above exemplifies the present invention it will of course be apparent that modifications are possible which pursuant to the patent statutes and laws do not depart from the spirit and scope of the protected invention.

We claim:

1. The method of controlling zebra mussels comprising contacting said mussels with an effective amount of an aqueous treating medium to kill the mussels or reduce the ability of the mussels to attach to a substrate or reduce the ability of the mussels to cluster, the medium comprising a powdered berry of a Phytolacca plant in water.

2. The method of claim 1 wherein said plant is *Phytolacca dodecandra*.

3. The method of claim 2 wherein said contacting is discontinued prior to the death of substantially all said mussels but is conducted for a sufficient period of time that surviving Zebra mussels have been weakened, after discontinuing the contact, as to their ability to attach to a substrate or to cluster with each other or both.

4. The method of claim 3 wherein said contacting is done for a sufficient period of time that at least about 70% of the mussels are dead after about 24 hours from initial contact and less than about 50% are dead at the time of discontinuing contact.

5. The method of claim 3 wherein less than about 50% of the mussels are dead at the time of discontinuing contact.

6. The method of claim 2 wherein said treating medium comprises a suspension of ground *Phytolacca dodecandra* berries.

7. The method of claim 1 wherein said contacting is done for at least 4 hours.

8. The method of claim 7 wherein said contacting is done for about 4 to about 8 hours.

9. The method of claim 1 wherein at least 50% of the mussels are killed during said contacting.

10. The method of killing a Zebra mussel comprising treating said mussel with a sufficient amount of a powdered berry of *Phytolacca dodecandra*.

11. The method of killing a zebra mussel or reducing the ability of the mussel to attach to a substrate, the method comprising treating said mussel with a sufficient amount to kill the mussel or reduce its ability to attach to a substrate of a molluscicidally effective portion of the berry of *hytolacca dodecandra* in an aqueous medium.

* * * * *